United States Patent

Hettiarachchi

[11] Patent Number: 5,904,991
[45] Date of Patent: May 18, 1999

[54] IN-SITU PALLADIUM DOPING OR COATING OF STAINLESS STEEL SURFACES

[75] Inventor: Samson Hettiarachchi, Menlo Park, Calif.

[73] Assignee: General Electric Company, Schenectady, N.Y.

[21] Appl. No.: 08/766,336

[22] Filed: Dec. 16, 1996

Related U.S. Application Data

[60] Division of application No. 08/635,593, Apr. 22, 1996, Pat. No. 5,818,893, which is a continuation-in-part of application No. 08/143,513, Oct. 29, 1993, abandoned.

[51] Int. Cl.⁶ ........................................... B32B 9/00
[52] U.S. Cl. ..................... 428/472.1; 376/305; 376/900
[58] Field of Search .................. 428/472.1; 376/305, 376/900; 106/1.21, 1.22, 1.24, 1.12, 1.15

[56] References Cited

U.S. PATENT DOCUMENTS

| | | | |
|---|---|---|---|
| 5,130,080 | 7/1992 | Niedrach | 376/305 |
| 5,130,081 | 7/1992 | Niedrach | 376/305 |
| 5,135,709 | 8/1992 | Andresen et al. | 376/305 |

FOREIGN PATENT DOCUMENTS

| | | |
|---|---|---|
| 0265723 | 5/1988 | European Pat. Off. . |
| 0450440 | 9/1991 | European Pat. Off. . |
| 0450444 | 9/1991 | European Pat. Off. . |
| 0514089 | 11/1992 | European Pat. Off. . |
| 0526160 | 2/1993 | European Pat. Off. . |
| 9218665 | 10/1992 | WIPO . |

OTHER PUBLICATIONS

Derwent Publications Ltd., London, GB, AN 84–059353 & JP–A–59 016 983 (Katayama Kagaku Kenkyushi), abstract.

*Primary Examiner*—David A. Simmons
*Assistant Examiner*—Robert R. Koehler
*Attorney, Agent, or Firm*—Nixon & Vanderhye

[57] ABSTRACT

An alloy component having an oxide film formed on its surface. The oxide film has atoms of a metal incorporated therein by a process comprising immersing the alloy surface in high-temperature water in which compound containing the metal is dissolved. The metal has the property of increasing the corrosion resistance of the alloy when incorporated in the oxide film. The compound has the property that it decomposes in the high-temperature water to release atoms of the metal which incorporate in the oxide film.

8 Claims, 5 Drawing Sheets

IN-SITU PALLADIUM DOPING OR COATING OF STAINLESS STEEL SURFACES

CROSS-REFERENCE TO RELATED APPLICATION

The present application is a Rule 60 Division of application Ser. No. 08/635,593, filed Apr. 22, 1996, now U.S. Pat. No. 5,818,893, which is a continuation-in-part application of application Ser. No. 08/143,513, filed Oct. 29, 1993 (incorporated by reference) and now abandoned.

FIELD OF THE INVENTION

This invention relates to reducing the corrosion potential of components exposed to high-temperature water. As used herein, the term "high-temperature water" means water having a temperature of about 150° C. or greater, steam, or the condensate thereof. High temperature water can be found in a variety of known apparatus, such as water deaerators, nuclear reactors, and steam-driven power plants.

BACKGROUND OF THE INVENTION

Nuclear reactors are used in central-station electric power generation, research and propulsion. A reactor pressure vessel contains the reactor coolant, i.e. water, which removes heat from the nuclear core. Respective piping circuits carry the heated water or steam to the steam generators or turbines and carry circulated water or feedwater back to the vessel. Operating pressures and temperatures for the reactor pressure vessel are about 7 MPa and 288° C. for a boiling water reactor (BWR), and about 15 MPa and 320° C. for a pressurized water reactor (PWR) The materials used in both BWRs and PWRs must withstand various loading, environmental and radiation conditions.

Some of the materials exposed to high-temperature water include carbon steel, alloy steel, stainless steel, nickel-based, cobalt-based and zirconium-based alloys. Despite careful selection and treatment of these materials for use in water reactors, corrosion occurs in the materials exposed to the high-temperature water. Such corrosion contributes to a variety of problems, e.g., stress corrosion cracking, crevice corrosion, erosion corrosion, sticking of pressure relief valves and buildup of the gamma radiation-emitting Co-60 isotope.

Stress corrosion cracking (SCC) is a known phenomenon occurring in reactor components, such as structural members, piping, fasteners, and welds, exposed to high-temperature water. As used herein, SCC refers to cracking propagated by static or dynamic tensile stressing in combination with corrosion at the crack tip. The reactor components are subject to a variety of stresses associated with, e.g., differences in thermal expansion, the operating pressure needed for the containment of the reactor cooling water, and other sources such as residual stress from welding, cold working and other asymmetric metal treatments. In addition, water chemistry, welding, heat treatment, and radiation can increase the susceptibility of metal in a component to SCC.

It is well known that SCC occurs at higher rates when oxygen is present in the reactor water in concentrations of about 5 ppb or greater. SCC is further increased in a high radiation flux where oxidizing species, such as oxygen, hydrogen peroxide, and short-lived radicals, are produced from radiolytic decomposition of the reactor water. Such oxidizing species increase the electrochemical corrosion potential (ECP) of metals. Electrochemical corrosion is caused by a flow of electrons from anodic to cathodic areas on metallic surfaces. The ECP is a measure of the thermodynamic tendency for corrosion phenomena to occur, and is a fundamental parameter in determining rates of, e.g., SCC, corrosion fatigue, corrosion film thickening, and general corrosion.

In a BWR, the radiolysis of the primary water coolant in the reactor core causes the net decomposition of a small fraction of the water to the chemical products $H_2$, $H_2O_2$, $O_2$ and oxidizing and reducing radicals. For steady-state operating conditions, equilibrium concentrations of $O_2$, $H_2O_2$, and $H_2$ are established in both the water which is recirculated and the steam going to the turbine. This concentration of $O_2$, $H_2O_2$, and $H_2$ is oxidizing and results in conditions that can promote intergranular stress corrosion cracking (IGSCC) of susceptible materials of construction. One method employed to mitigate IGSCC of susceptible material is the application of hydrogen water chemistry (HWC), whereby the oxidizing nature of the BWR environment is modified to a more reducing condition. This effect is achieved by adding hydrogen gas to the reactor feedwater. When the hydrogen reaches the reactor vessel, it reacts with the radiolytically formed oxidizing species to reform water, thereby lowering the concentration of dissolved oxidizing species in the water in the vicinity of metal surfaces. The rate of these recombination reactions is dependent on local radiation fields, water flow rates and other variables.

The injected hydrogen reduces the level of oxidizing species in the water, such as dissolved oxygen, and as a result lowers the ECP of metals in the water. However, factors such as variations in water flow rates and the time or intensity of exposure to neutron or gamma radiation result in the production of oxidizing species at different levels in different reactors. Thus, varying amounts of hydrogen have been required to reduce the level of oxidizing species sufficiently to maintain the ECP below a critical potential required for protection from IGSCC in high-temperature water. As used herein, the term "critical potential" means a corrosion potential at or below a range of values of about −230 to −300 mV based on the standard hydrogen electrode (SHE) scale. IGSCC proceeds at an accelerated rate in systems in which the ECP is above the critical potential, and at a substantially lower or zero rate in systems in which the ECP is below the critical potential. Water containing oxidizing species such as oxygen increases the ECP of metals exposed to the water above the critical potential, whereas water with little or no oxidizing species presents results in an ECP below the critical potential.

Corrosion potentials of stainless steels in contact with reactor water containing oxidizing species can be reduced below the critical potential by injection of hydrogen into the water so that the dissolved hydrogen concentration is about 50 to 100 ppb or greater. For adequate feedwater hydrogen addition rates, conditions necessary to inhibit IGSCC can be established in certain locations of the reactor. Different locations in the reactor system require different levels of hydrogen addition. Much higher hydrogen injection levels are necessary to reduce the ECP within the high radiation flux of the reactor core, or when oxidizing cationic impurities, e.g., cupric ion, are present.

It has been shown that IGSCC of Type 304 stainless steel (composition in weight % 18.0–20.0 Cr, 8.0–10.0 Ni, 2.00 Mn, 1.0 Si, 0.08 C, 0.08 S, 0.045 P) used in BWRs can be mitigated by reducing the ECP of the stainless steel to values below −0.230 V(SHE). An effective method of achieving this objective is to use HWC. However, high hydrogen additions, e.g., of about 200 ppb or greater, that may be required to reduce the ECP below the critical potential, can result in a higher radiation level in the steam-driven turbine section from incorporation of the short-lived N-16 species in the steam. For most BWRs, the amount of hydrogen addition required to provide mitigation of IGSCC of pressure vessel internal components results in an increase in the main steam line radiation monitor by a factor of five. This increase in main steam line radiation can cause high, even unacceptable, environmental dose rates that can require expensive investments in shielding and radiation exposure control. Thus, recent investigations have focused on using minimum levels of hydrogen to achieve the benefits of HWC with minimum increase in the main steam radiation dose rates.

An effective approach to achieve this goal is to either coat or alloy the stainless steel surface with palladium or any other platinum group metal. The presence of palladium on the stainless steel surface reduces the hydrogen demand to reach the required IGSCC critical potential of −0.230 V(SHE). The techniques used to date for palladium coating include electroplating, electroless plating, plasma deposition and related high-vacuum techniques. Palladium alloying has been carried out using standard alloy preparation techniques. Both of these approaches are ex situ techniques in that they cannot be practiced while the reactor is in operation.

U.S. Pat. No. 5,135,709 to Andresen et al. discloses a method for lowering the ECP on components formed from carbon steel, alloy steel, stainless steel, nickel-based alloys or cobalt-based alloys which are exposed to high-temperature water by forming the component to have a catalytic layer of a platinum group metal. As used therein, the term "catalytic layer" means a coating on a substrate, or a solute in an alloy formed into the substrate, the coating or solute being sufficient to catalyze the recombination of oxidizing and reducing species at the surface of the substrate; and the term "platinum group metal" means metals from the group consisting of platinum, palladium, osmium, ruthenium, iridium, rhodium, and mixtures thereof.

In nuclear reactors, ECP is further increased by higher levels of oxidizing species, e.g., up to 200 ppb or greater of oxygen in the water, from the radiolytic decomposition of water in the core of the nuclear reactor. The method disclosed in U.S. Pat. No. 5,135,709 further comprises providing a reducing species in the high-temperature water that can combine with the oxidizing species. In accordance with this known method, high concentrations of hydrogen, i.e., about 100 ppb or more, must be added to the water to provide adequate protection to materials outside the reactor core region, and still higher concentrations are needed to afford protection to materials in the reactor core. It is also known that platinum or palladium can be added to increase the ECP of stainless steel exposed to deaerated acidic aqueous solutions, thereby forming a passive oxide layer on the stainless steel and reducing further corrosion.

The formation of a catalytic layer of a platinum group metal on an alloy from the aforementioned group catalyzes the recombination of reducing species, such as hydrogen, with oxidizing species, such as oxygen or hydrogen peroxide, that are present in the water of a BWR. Such catalytic action at the surface of the alloy can lower the ECP of the alloy below the critical potential where IGSCC is minimized. As a result, the efficacy of hydrogen additions to high-temperature water in lowering the ECP of components made from the alloy and exposed to the injected water is increased manyfold. Furthermore, it is possible to provide catalytic activity at metal alloy surfaces if the metal substrate of such surfaces contains a catalytic layer of a platinum group metal. Relatively small amounts of the platinum group metal are sufficient to provide the catalytic layer and catalytic activity at the surface of the metal substrate. For example, U.S. Pat. No. 5,135,709 teaches that a solute in an alloy of at least about 0.01 wt. %, preferably at least 0.1 wt. %, provides a catalytic layer sufficient to lower the ECP of the alloy below the critical potential. The solute of a platinum group metal can be present up to an amount that does not substantially impair the metallurgical properties, including strength, ductility, and toughness of the alloy. The solute can be provided by methods known in the art, for example by addition to a melt of the alloy or by surface alloying. In addition, a coating of the platinum group metal, or a coating of an alloy comprised of a solute of the platinum group metal as described above, provides a catalytic layer and catalytic activity at the surface of the metal. Suitable coatings can be deposited by methods well known in the art for depositing substantially continuous coatings on metal substrates, such as plasma spraying, flame spraying, chemical vapor deposition, physical vapor deposition processes such as sputtering, welding such as metal inert gas welding, electroless plating, and electrolytic plating.

Thus, lower amounts of reducing species such as hydrogen are effective to reduce the ECP of the metal components below the critical potential, because the efficiency of recombination of oxidizing and reducing species is increased manyfold by the catalytic layer. Reducing species that can combine with the oxidizing species in the high-temperature water are provided by conventional means known in the art. In particular, reducing species such as hydrogen, ammonia, or hydrazine are injected into the feedwater of the nuclear reactor.

SUMMARY OF THE INVENTION

The present invention is a technique of improving the corrosion resistance of metal surfaces disposed in high temperature water by introducing into the water small amounts of a metal-containing compound capable of imparting improved corrosion resistance. The metal-containing compound is introduced in the absence of hydrogen or other added reducing agents, and is added in an amount such that, upon decomposition of the metal-containing compound in the high temperature water, the metal atoms are released in an amount sufficient, when present on the metal components, to reduce the electrochemical corrosion potential of the metal components to a level below the critical potential and thereby protect against intergranular stress corrosion cracking.

In one aspect, the invention provides a method for reducing corrosion of alloy components in a water-cooled nuclear reactor or associated components having an oxide film formed on the surface thereof. The method comprises the step of injecting into the water of the reactor a solution of a compound containing a metal which increases the corrosion resistance of stainless steel when present in the oxide film. The compound has the property that it decomposes under operating reactor thermal conditions to release atoms of the metal which incorporate in the oxide film.

In another aspect, there is provided a method for reducing corrosion of alloy components in a water-cooled nuclear reactor or associated components, wherein a solution of a compound containing a metal is injected into the water of said reactor in an amount such that, upon decomposition of the compound under the operating reactor thermal conditions, atoms of the metal compound are released at a rate such that the concentration of the metal in the water is sufficient, once doped on the alloy components, to reduce the electrochemical corrosion potential of the alloy components to a level below the critical potential. In this way, the metal components are protected against intergranular stress corrosion cracking.

In a further aspect, there is provided an alloy component having on its surface an oxide film doped with atoms of a metal capable of increasing the corrosion resistance of the alloy when incorporated in the oxide film. The metal atoms are incorporated in the oxide film by a process wherein the alloy is immersed in high-temperature water in which the compound containing a metal is dissolved. The compound has the property that it decomposes in the high-temperature water to release atoms of the metal which incorporate in the oxide film.

Compounds of the platinum group metals are preferred for this purpose. The term "platinum group metal" as used herein means platinum, palladium, osmium, ruthenium, iridium, rhodium and mixtures thereof. It is also possible to use compounds of non-platinum group metals, such as for example zinc, titanium, zirconium, niobium, tantalum, tungsten and vanadium. Mixtures of platinum group compounds may be used. Mixtures of platinum group compounds and non-platinum group compounds may also be used, for example platinum and zinc. The compounds may be organometallic, organic or inorganic and may be soluble or insoluble in water (i.e. may form solutions or suspensions in water). Generally, when mixtures of platinum and non-platinum group metals are used, the platinum group metal is in excess of the other metal.

Examples of preferred platinum group metal compounds which may be used are palladium acetyl acetonate, palladium nitrate, palladium acetate, platinum acetyl acetonate, hexahydroxyplatinic acid, $Na_2Pt(OH)_6$, $Pt(NH_3)_4(NO_3)_2$, $K_3Ir(NO_2)_6$ and $K_3Rh(NO_2)_6$. Other examples are platinum (IV) oxide ($Pt(IV)O_2$), platinum(IV) oxide-hydrate ($Pt(IV)O_2.xH_2O$, where x is 1–10), rhodium(II) acetate ($Rh(II)ac_2$), Rh(III) nitrate ($Rh(III)(NO_3)_3$), rhodium(III) oxide ($Rh(III)_2O_3$), rhodium(III) oxide-hydrate ($Rh(III)_2O_3.xH_2O$, where x is 1–10), rhodium(II) phosphate ($Rh(III)PO_4$) and rhodium (III) sulphate ($Rh(III)_2(SO_4)_3$). Palladium acetyl acetonate and palladium nitrate are particularly preferred.

Examples of mixtures of the compounds which may be used are mixtures containing platinum and iridium, and platinum and rhodium. Use of such mixtures results in incorporation on the oxided stainless steel surfaces of both noble metals. The presence of iridium or rhodium with the platinum gives good long-term durability. It has been found that a combination of about 40–80 ppb Pt and 10–35 ppb Rh, for example about 60 ppb Pt and about 20 ppb Rh, provides good adherent properties over extended periods of time.

The metal compound is injected in situ in the form of an aqueous solution or suspension. As used in the claims hereafter, the term "solution" means solution or suspension. When the metal compound solution or suspension enters the high-temperature water, the compound decomposes very rapidly to produce atoms/ions, and the metal (or metals) is incorporated into the metal (typically stainless steel) oxide film. In accordance with the process, only the solution or suspension of the compound is introduced into the high-temperature water initially. No further agents, such as hydrogen, other reducing agents, acids or bases are introduced into the high-temperature water when the compound solution or suspension is injected into and decomposes in the high-temperature water.

The process of the present invention is distinguished from the processes of U.S. Pat. Nos. 5,130,080 and 5,130,181 to Niedrach. The Niedrach patents teach that it is possible to electrolessly plate oxide films using conventional electroless plating techniques. Conventional electroless plating is carried out at relatively low temperatures, typically in the region of 50 to 80° C., possibly lower, and requires the presence of an added reducing agent, typically sodium hypophosphite, to supply electrons for reduction of the noble metal ions to the metal. The reaction takes place only on a catalytic surface which has been sensitized/activated beforehand, for example with stannous chloride, and the process results in a build-up of metal coating on the surface which eventually coats the entire surface with deposited metal. The electroless plating bath typically contains high ionic concentrations, of the order of thousands of ppm, of chemicals, including, for example, palladium (II) chloride, ammonium hydroxide, ammonium chloride, disodium EDTA and hydrazine, as well as a reducing agent (e.g. sodium hypophosphite). The pH of the electroless bath is usually in the region of 9.0 to 10.5 in view of the presence of base (ammonium hydroxide and ammonium chloride).

The process of the present invention does not rely on the use of electroless plating techniques or other techniques which result in the metal being plated on the oxide surface. In the present process, the metal compound or mixture of metal compounds is introduced into the high-temperature water in an amount such that the concentration of the metal(s) in the water is very low, i.e. in the ppb range, but is sufficient such that when present on the metal component, the ECP is lowered below the critical potential required for protection from stress corrosion cracking. Typically, the metal compound is added in such an amount to produce a metal concentration of no higher than 2000 ppb, for example 0.1 to 1000 ppb, typically 1 to 500 ppb, more usually 5 to 100 ppb.

The compound solution or suspension is injected into the high-temperature water while the reactor is operating and generating nuclear heat. The temperature of the water when the reactor is operating is typically in the range of 150–300° C., for example 190–290° C., more usually about 288° C. When the compound meets the high-temperature water, it decomposes very rapidly and the metal atoms are incorporated in the oxide surface.

At the very low levels of metal(s) introduced into the reactor, the stainless steel oxide surface is not covered completely with metal. Typically, the doped surface has metal present in an amount of about 0.1–15 atomic %, for example 0.5–10 atomic %, more usually 2–5 atomic %.

The depth of metal in the doped surface is generally in the range of 100 to 1000 Angstroms, more usually 200 to 500 Angstroms. The external appearance of the doped oxided alloy treated according to the present process does not differ significantly from the appearance of untreated stainless steel oxide. The doped surface does not have a bright metallic luster as is generally obtained with electroplating or electroless coating processes.

In the present process, only the compound solution or suspension is injected into the high-temperature water. No reducing agents (including hydrogen), acids and bases, are added. As a result, the pH of the water at lower temperatures is in the region of 6.5 to 7.1, and at higher operating temperatures is lower, generally in the region of about 5.5–5.8, for example 5.65. This is due to increased dissociation of the water at the higher temperatures.

An operating BWR has very stringent coolant water conductivity levels which must be observed. Typically, the conductivity of the coolant water must not exceed 0.3 $\mu$S/cm, and more usually must be less than 0.1 $\mu$S/cm. Such conductivity levels are adversely impacted by high ionic concentrations of species, and every effort is made in the present process to ensure that reactor ionic concentrations of species are maintained as low as possible after clean-up, preferably less than 5 ppb. The process in particular excludes the use of chloride ion in view of its corrosive nature.

The present process does not involve any catalytic activation/sensitization of the stainless steel oxide surface. The use of stannous chloride to achieve such activation would be incompatible with operation of the BWR and the stringent conductivity limits on the coolant water referred to above.

While not being bound by theory, it is understood that the metal, for example palladium, is incorporated into the stainless steel oxide film via a thermal decomposition process of the compound wherein metal ions/atoms apparently replace iron, nickel and/or chromium atoms in the oxide film, resulting in a metal-doped oxide film. The metal, such as palladium, may for example be incorporated within or on the surface of the oxide film and may be in the form of a finely divided metal. The oxide film is believed to include mixed nickel, iron and chromium oxides.

The ECPs of the stainless steel components all drop by approximately 300 mV after injection of the noble metal. It is possible to reduce the ECP of Type 304 stainless steel to IGSCC protection values without injecting hydrogen when an organic metal compound has been injected into the water. The catalytic oxidation of organics on palladium-doped surfaces consumes oxygen, thereby lowering the dissolved oxygen content in the high temperature water. Good results are also obtained when an inorganic metal compound(s) is used. Moreover, clean-up of the water is easier when inorganic(s) such as nitrates are used as compared to organics such as formates and acetates. For this reason, inorganic compounds, particularly inorganic platinum group metal inorganic compounds (e.g. palladium nitrate), are typically used.

Following injection and incorporation of the metal(s) in the oxided stainless steel surfaces, the water is subjected to a conventional clean-up process to remove ionic materials such as nitrate ions present in the water. This clean-up process is usually carried out by passing a fraction of the water removed from the bottom head of the reactor and recirculation piping through an ion exchange resin bed, and the treated water is then returned to the reactor via the feedwater system. Hydrogen may subsequently be introduced into the water some time after the doping reaction, for example 1 to 72 hours after injection and incorporation of the metal atoms in the oxided surface, to catalyze recombination of hydrogen and oxygen on the metal doped surfaces. As hydrogen is added, the potential of the metal-doped oxide film on the stainless steel components is reduced to values which are much more negative than when hydrogen is injected into a BWR having stainless steel components which are not doped with the noble metal.

In summary, the oxygen content of the reactor water can be reduced by injection of a platinum group metal compound alone initially into high temperature water to give oxided stainless steel surfaces doped with the platinum group metal(s). Some oxygen will be reduced by the organics of the metal compound (e.g. an organometallic palladium compound) following thermal decomposition or radiolytic decomposition (induced by gamma and neutron radiation) of the metal compound. Subsequent introduction of hydrogen, after the doping reaction, will reduce the amount of oxygen as a result of the recombination of dissolved oxygen and hydrogen molecules at the platinum group metal-doped surfaces forming water molecules.

DETAILED DESCRIPTION OF PREFERRED EMBODIMENTS

Figure 1:
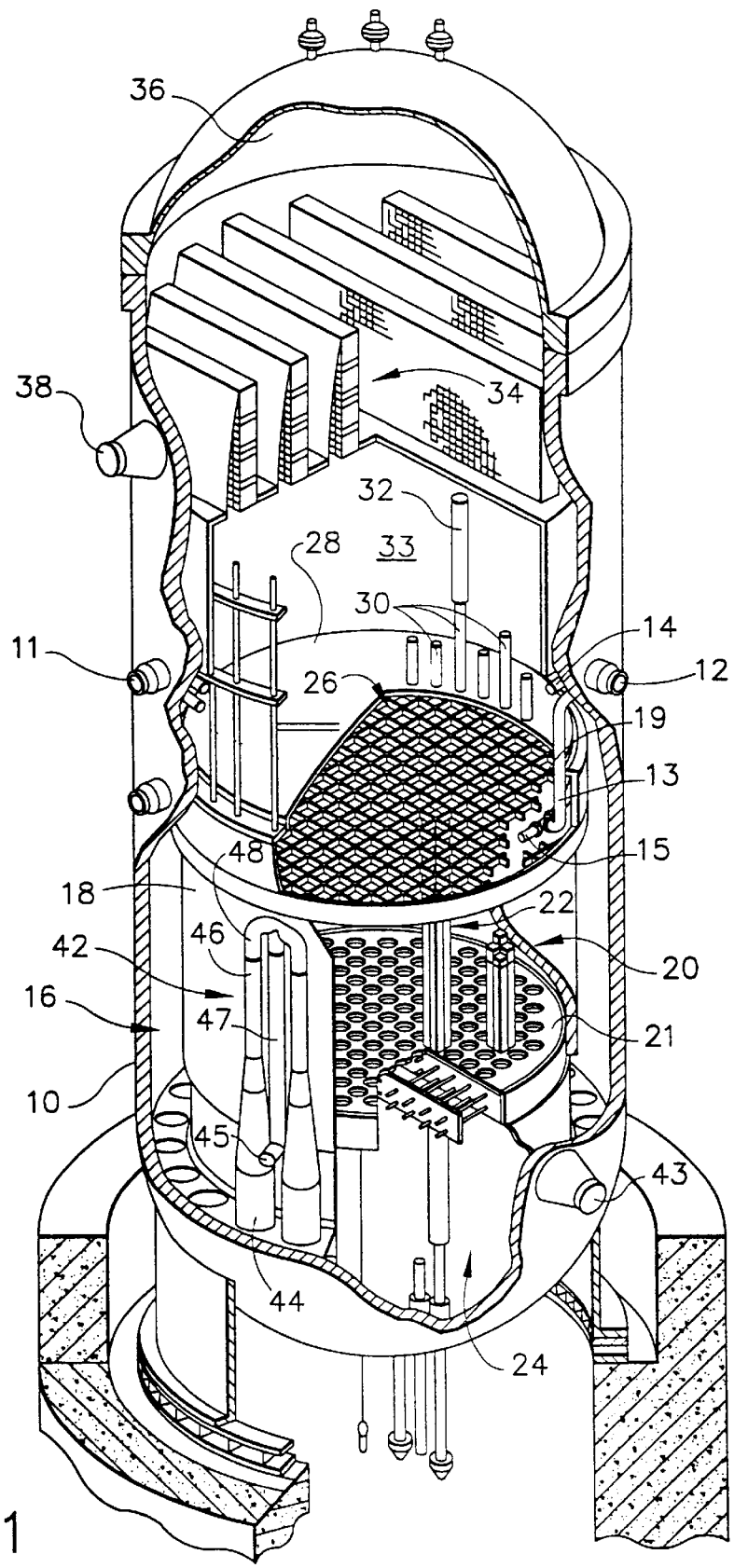
FIG. 1 is a schematic showing a partially cutaway perspective view of a conventional BWR.

The fluid flow in a boiling water reactor will be generally described with reference to FIG. 1. Feedwater is admitted into a reactor pressure vessel (RPV) 10 via a feedwater inlet 12 and a feedwater sparger 14, which is a ring-shaped pipe having suitable apertures for circumferentially distributing the feedwater inside the RPV. A core spray inlet 11 supplies water to a core spray sparger 15 via core spray line 13. The feedwater from feedwater sparger 14 flows downwardly through the downcomer annulus 16, which is an annular region between RPV 10 and core shroud 18. Core shroud 18 is a stainless steel cylinder which surrounds the core 20 comprising numerous fuel assemblies 22 (only two 2×2 arrays of which are depicted in FIG. 1). Each fuel assembly is supported at the top by top guide 19 and at the bottom by core plate 21. Water flowing through downcomer annulus 16 then flows to the core lower plenum 24.

The water subsequently enters the fuel assemblies 22 disposed within core 20, wherein a boiling boundary layer (not shown) is established. A mixture of water and steam enters core upper plenum 26 under shroud head 28. Core upper plenum 26 provides standoff between the steam-water mixture exiting core 20 and entering vertical standpipes 30, which are disposed atop shroud head 28 and in fluid communication with core upper plenum 26.

The steam-water mixture flows through standpipes 30 and enters steam separators 32, which are of the axial-flow centrifugal type. The separated liquid water then mixes with feedwater in the mixing plenum 33, which mixture then returns to the core via the downcomer annulus. The steam passes through steam dryers 34 and enters steam dome 36. The steam is withdrawn from the RPV via steam outlet 38.

The BWR also includes a coolant recirculation system which provides the forced convection flow through the core necessary to attain the required power density. A portion of the water is sucked from the lower end of the downcomer annulus 16 via recirculation water outlet 43 and forced by a centrifugal recirculation pump (not shown) into jet pump assemblies 42 (only one of which is shown) via recirculation water inlets 45. The BWR has two recirculation pumps, each of which provides the driving flow for a plurality of jet pump assemblies. The pressurized driving water is supplied to each jet pump nozzle 44 via an inlet riser 47, an elbow 48 and an inlet mixer 46 in flow sequence. A typical BWR has 16 to 24 inlet mixers.

The present invention is a technique to dope oxided stainless steel surfaces with low concentrations of one or more metals. In the following discussion, for convenience of description, reference will be made to the use of palladium. It is understood however that the invention is not limited to the use of palladium and other platinum group and/or non-platinum group metals may be used alone or as mixtures.

The palladium-containing compound is injected in situ into the high-temperature water of a BWR in an amount such as to produce, upon decomposition of the compound, a metal concentration of up to 2000 ppb, for example about 1 to 850 ppb, more usually 5 to 100 ppb. Preferably, the palladium compound is injected at a point downstream of the recirculation water outlet 43 (see FIG. 1) . The high temperatures as well as the gamma and neutron radiation in the reactor core act to decompose the compound, thereby freeing palladium ions/atoms for deposition on the surface of the oxide film. One palladium-containing compound successfully used for this purpose is the organometallic compound, palladium acetylacetonate. However, other palladium compounds of organic, organometallic and inorganic nature can be used for this purpose, as exemplified above.

Tests were conducted which proved that the present method for incorporating palladium in the stainless steel surfaces of a BWR is feasible. Moreover, it has been shown that after palladium treatment in accordance with the invention, the ECP value of the stainless steel surfaces remains quite negative and below the required IGSCC protection potential of −0.230 V(SHE) even without the addition of any hydrogen when organics are present in the water. This phenomenon has been neither reported nor observed previously. Thus, the invention consists of two parts: (1) an in situ method for doping oxided stainless steel surfaces with palladium (or other metal) at low concentrations while the reactor is operating; and (2) a method that makes the IGSCC protection potential achievable on noble metal doped surfaces without injecting hydrogen into the water. If an inorganic metal compound is used for the doping process, hydrogen is subsequently added to lower the ECP and hence achieve the IGSCC protection potential.

An experiment was performed to determine the feasibility of depositing palladium on Type 304 stainless steel by injecting palladium acetylacetonate, into an autoclave that formed part of a high-temperature recirculating flow loop. The autoclave had a constant extension rate tensile (CERT) test specimen made of Type 304 stainless steel and a stainless steel tip electrode also made of Type 304 stainless steel. The reference electrodes used to measure ECPs consisted of a $Cu/Cu_2O/ZrO_2$ type reference electrode and an external pressure balanced Ag/AgCl, 0.1M KCl reference electrode. The recirculating flow loop contained deionized water heated to 550° F. inside the autoclave. The oxygen level in the effluent water was 170 ppb and the CERT specimen potential at this oxygen level was +0.042 V(SHE).

The palladium acetylacetonate injection solution was prepared by dissolving 52.6 mg of palladium acetylacetonate powder in 40 ml of ethanol. The ethanol solution is then diluted with water. After dilution, 10 ml of ethanol are added to the solution. This is then diluted to a volume of 1 liter. Alternatively, a water-based suspension can be formed, without using ethanol, by mixing palladium acetylacetonate powder in water. The palladium acetylacetonate compound, dissolved in the ethanol/water mixture, was injected into the inlet side of the main pump in the flow loop using an injection pump at a rate of 0.4 cc/min so that the solution entering the autoclave (at 550° F.) had a palladium concentration of approximately 50 ppb.

Figure 2:
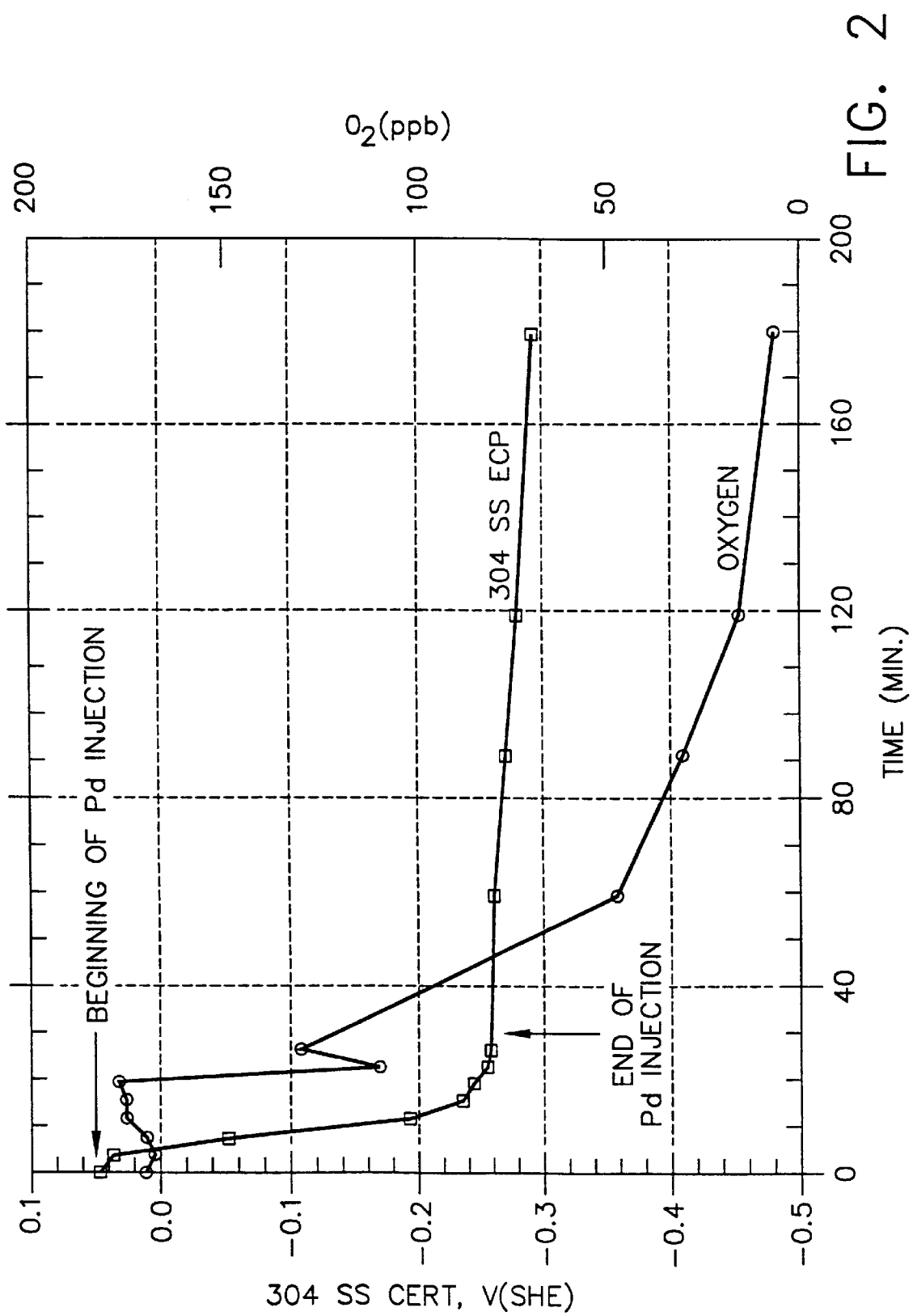
FIG. 2 is a plot showing the variation of the oxygen level of effluent water and the specimen ECP over time during and after the injection of palladium into an autoclave forming a part of a high-temperature recirculating flow loop.

As the palladium was being injected, within 30 minutes the ECP of the Type 304 stainless steel CERT sample dropped from +0.042 V(SHE) to −0.256 V(SHE). The effluent oxygen content also dropped as palladium was getting into the loop. The palladium injection was stopped after 30 minutes, but the ECP of the Type 304 stainless steel CERT specimen continued to drop slowly with time (see FIG. 2). The effluent oxygen content also continued to drop to sub-ppb levels despite the fact that the dissolved oxygen in the inlet water was approximately 320 ppb (calculated from the gas composition). During the palladium injection time, the stainless steel tip electrode potential dropped from −0.007 V(SHE) to −0.329 V(SHE), and the autoclave potential dropped from +0.048 V(SHE) to −0.257 V(SHE). In all cases the potentials continued to drop slowly even after the palladium injection had been discontinued.

The following conclusions were drawn from the experimental data:

(1) The palladium either deposits or is incorporated into the stainless steel oxide film via a thermal decomposition process of the organometallic compound. As a result of that decomposition, palladium ions/atoms become available to replace atoms, e.g., iron atoms, in the oxide film, thereby producing a palladium-doped oxide film on stainless steel. As used in the claims hereafter, the term "atoms" means ions or atoms.

(2) The potentials of the Type 304 stainless steel CERT specimen, the Type 304 stainless steel electrode tip and the autoclave all dropped by approximately 300 mV after palladium injection.

(3) Although the oxygen content of the water entering the loop was high (approximately 320 ppb), the effluent oxygen content dropped to sub-ppb levels because oxygen was consumed by the organics at the noble metal doped hot stainless steel surfaces. The organics were oxidized to form acetates/formates, as confirmed by ion chromatography.

(4) It is possible to reduce the potential of Type 304 stainless steel to IGSCC protection values without using hydrogen if organics are present in the water. This is more effective on palladium-doped stainless steel surfaces.

Figure 3:
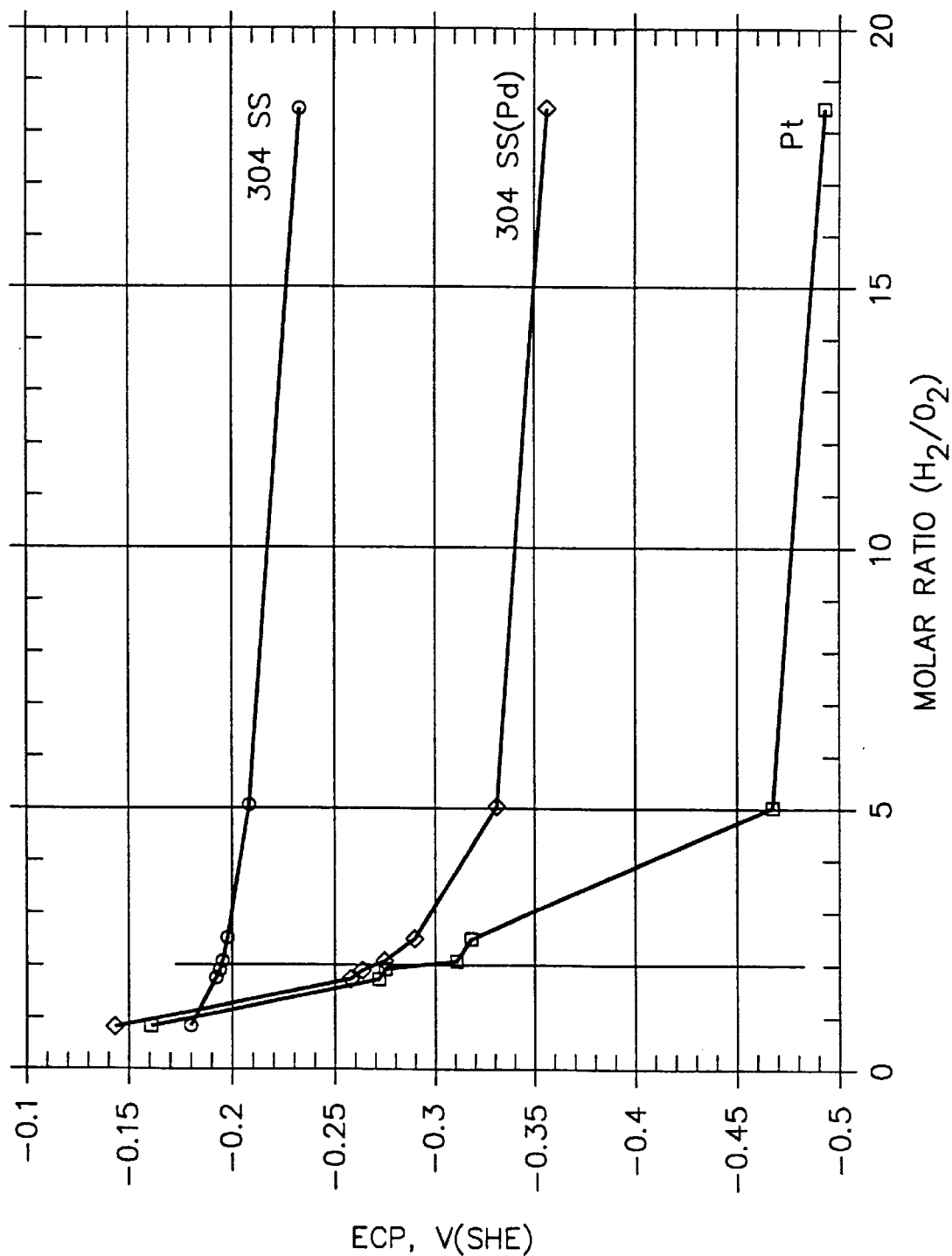
FIG. 3 is a plot showing the ECPs of platinum, oxidized Type 304 stainless steel and palladium-doped Type 304 stainless steel as a function of the molar ratio of hydrogen to oxygen. In this case, palladium doping was performed for 30 minutes.

(5) The ECPs for platinum, palladium-doped Type 304 stainless steel (30 minutes of Pd injection) and lightly oxidized Type 304 stainless steel without palladium doping were determined as a function of the molar ratio of $H_2$ to $O_2$ dissolved in water. As can be seen in FIG. 3, the ECP for palladium-doped Type 304 stainless steel goes more negative than the ECP for undoped Type 304 stainless steel as the amount of $H_2$ increases. However, the ECP for the doped stainless steel was not as low as the ECP for platinum. The ECP for palladium-doped Type 304 stainless steel is below the critical potential when the molar ratio of $H_2/O_2=2$, at which point the palladium doping is not yet optimized.

Figure 4:
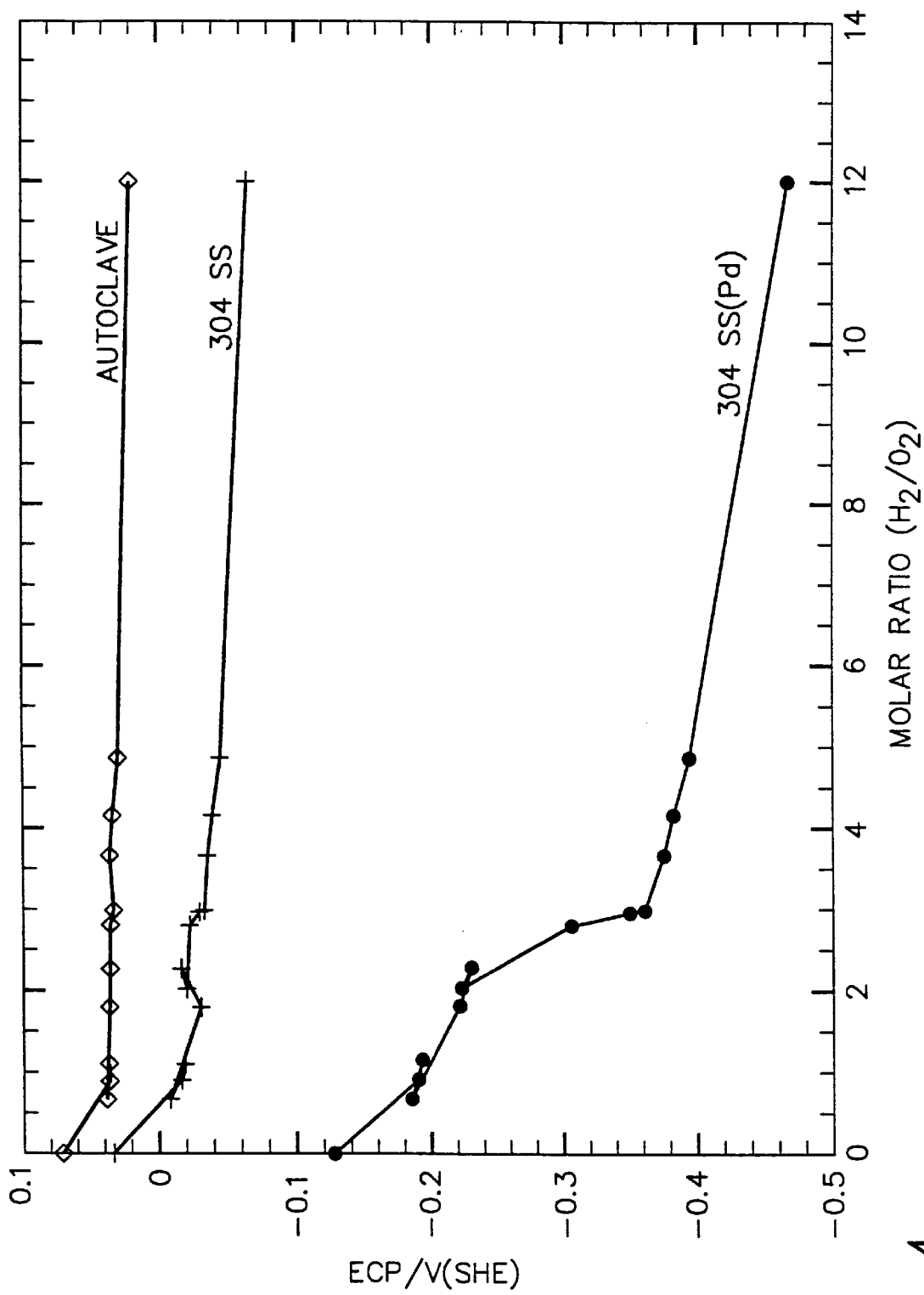
FIG. 4 is a plot showing the ECPs of well oxidized Type 304 stainless steel, palladium-doped Type 304 stainless steel and a Type 304 stainless steel autoclave as a function of the molar ratio of hydrogen to oxygen. In this case, palladium doping was performed for 48 hr.

(6) The ECPs for a Type 304 stainless steel autoclave, palladium-doped Type 304 stainless steel (48 hr of Pd injection) and well-oxidized Type 304 stainless steel without palladium doping were determined as a function of the molar ratio of $H_2$ to $O_2$ dissolved in water. As can be seen in FIG. 4, the ECP for Pd-doped Type 304 stainless steel goes more negative than the ECP for undoped Type 304 stainless steel as the amount of $H_2$ increases.

Figure 5:
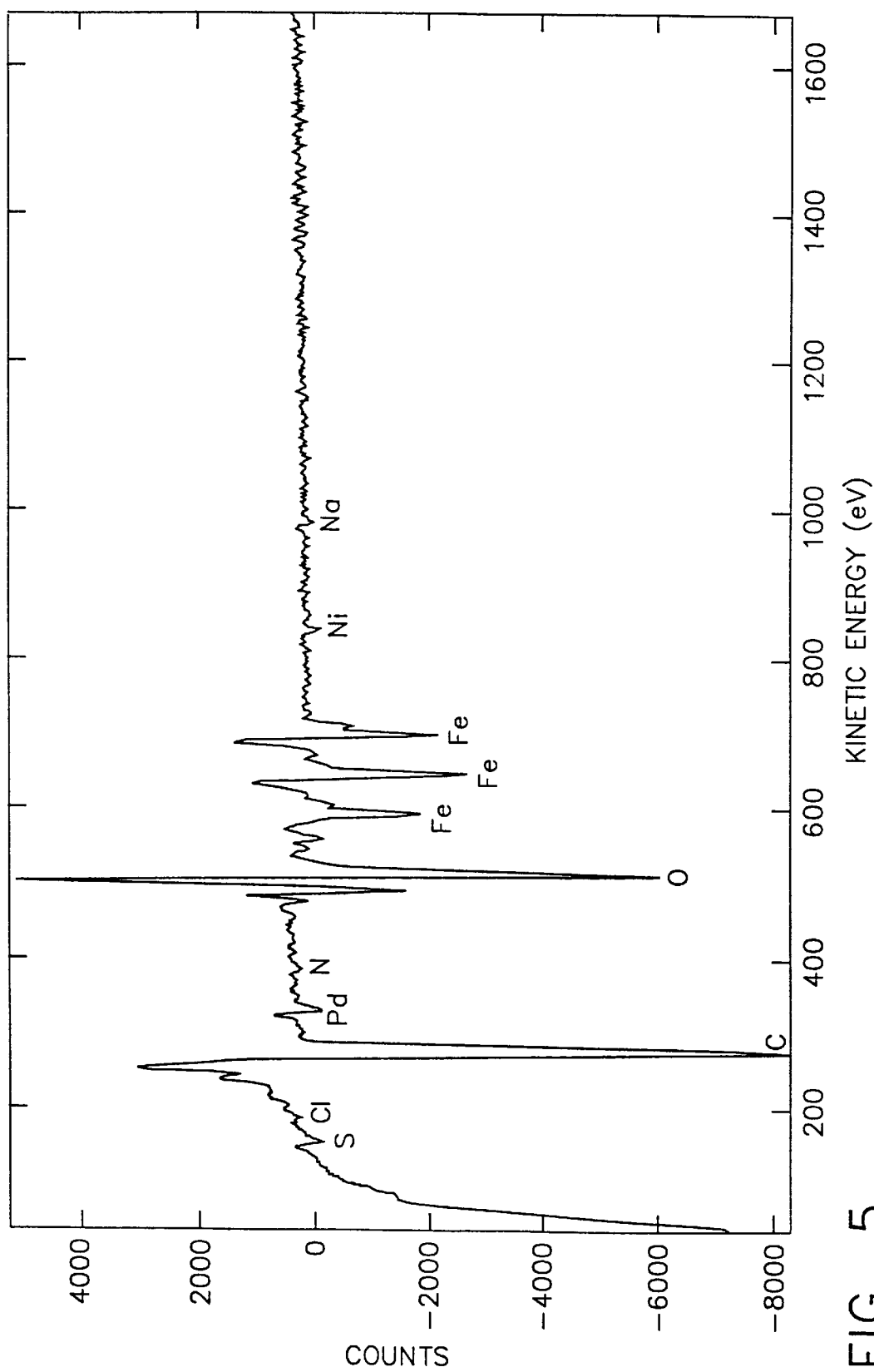
FIG. 5 shows an analysis of the Type 304 stainless steel surface after palladium doping for 48 hr.

(7) The data in FIG. 5 confirm the presence of palladium on the surface of the Type 304 stainless steel doped with palladium for 48 hr. Table I provides the surface concentration of palladium, which is 0.8 atomic %, and other elements for stainless steel doped with palladium for 48 hr. The dashes indicate no observation of a signal.

TABLE I

| Spectrum No. | Etch Depth | Na | Ni | Fe | Cr | O | N | Pd | C | Cl | S | Al |
|---|---|---|---|---|---|---|---|---|---|---|---|---|
| 1 | 0 | 0.5 | 0.8 | 15 | — | 21 | 0.8 | 0.8 | 61 | 0.1 | 0.5 | — |
| 2 | 1000 Å | — | 3.6 | 37 | 7.0 | 46 | — | — | 1.5 | — | — | 5.2 |

The present invention offers the advantage that Type 304 stainless steel surfaces can be doped wit h palladium using an in situ technique (while the reactor is operating) which is simple in application and also inexpensive. However, the technique is not limited to in situ application. The application technology can be implemented even for doping ex situ components. The technique can be applied to operating BWRs and PWRs and their associated components, such as steam generators. In practice, the palladium concentration in the reactor water is preferably in the range of 1 to 1000 ppb, for example 2 to 900 ppb, more usually 5 to 100 ppb.

The invention is advantageous in that IGSCC critical potential can be achieved without the addition of hydrogen when organics are present in the water. Furthermore, when hydrogen is added, as when inorganics are present, the amount of hydrogen needed is minimized so that the main steam line radiation dose rates do not reach undesirable levels. The technology of the invention is unique because it can be applied during operation of a reactor and is simple when compared with other standard technologies such as electroplating, electroless plating, and plasma deposition, which require reducing agents, surface activation, complex chemical formulations, complex equipment and tooling.

The foregoing method has been disclosed for the purpose of illustration. Variations and modifications of the disclosed method will be readily apparent to practitioners skilled in the art of hydrogen water chemistry. For example, metals other than palladium can be applied using this technique, e.g., other platinum group metals. A platinum group metal can be injected in the form of an organic or organometallic compound to reduce the potential of stainless steel reactor components even in the absence of hydrogen injection. Alternatively, the platinum group metal can be injected in the form of an inorganic compound to reduce the potential of stainless steel reactor components. It may also be possible to dope oxide films on stainless steel components with non-platinum group metals, e.g., zirconium and titanium, using the technique of the invention. Furthermore, the metal acetylacetonate need not be injected as part of an ethanol/water solution. Instead, the metal acetylacetonate powder can be mixed with water alone to form a suspension which is injected into the reactor water. To improve the stability of the suspension, ultrasonication may be used to break down the particles. All such variations and modifications are intended to be encompassed by the claims set forth hereinafter.

I claim:

1. An alloy component having an oxide film formed on its surface, said oxide film having atoms of a metal incorporated therein by a process comprising the step of immersing said alloy surface in high-temperature water in which a compound containing said metal is dissolved, said metal having the property of increasing the corrosion resistance of said alloy when incorporated in said oxide film, said compound having the property that it decomposes in said high-temperature water to release atoms of said metal which incorporate in said oxide film.

2. The alloy component as defined in claim 1, wherein said metal is a platinum group metal.

3. The alloy component as defined in claim 2, wherein said platinum group metal is palladium.

4. The alloy component as defined in claim 1, wherein a mixture of palladium and rhodium is used.

5. An alloy component according to claim 1, wherein the metal is present in the oxide layer in an amount of about 0.1–15 atomic percent.

6. A component according to claim 5, wherein the metal is present in the oxide surface in an amount of about 2–5 atomic percent.

7. An alloy component according to claim 1, wherein the depth of metal incorporated into the oxide surface is in the range of 100–1,000 Angstroms.

8. An alloy component according to claim 7, wherein the metal incorporated into the surface is at a depth of about 200–500 Angstroms.

* * * * *